(12) United States Patent
Lazea et al.

(10) Patent No.: US 12,339,267 B2
(45) Date of Patent: Jun. 24, 2025

(54) SYSTEM AND METHOD FOR SIMULTANEOUSLY EXAMINING, MAINTAINING AND CALIBRATING MULTIPLE SENSORS AND SENSOR TYPES

(71) Applicant: Aircuity, Inc., Norwood, MA (US)

(72) Inventors: George Lazea, Newton, MA (US); Andrew Szabo, Charlton, MA (US)

(73) Assignee: Aircuity, Inc., Norwood, MA (US)

( * ) Notice: Subject to any disclaimer, the term of this patent is extended or adjusted under 35 U.S.C. 154(b) by 344 days.

(21) Appl. No.: 17/934,557

(22) Filed: Sep. 22, 2022

(65) Prior Publication Data

US 2024/0102983 A1    Mar. 28, 2024

(51) Int. Cl.
| | |
|---|---|
| G01N 1/26 | (2006.01) |
| G01N 33/00 | (2006.01) |
| G01N 35/10 | (2006.01) |
| G01N 37/00 | (2006.01) |

(52) U.S. Cl.
CPC ..... *G01N 33/0075* (2013.01); *G01N 33/0006* (2013.01); *G01N 33/0016* (2013.01); *G01N 33/0067* (2013.01)

(58) Field of Classification Search
CPC .................................................. G01N 33/0006
See application file for complete search history.

(56) References Cited

U.S. PATENT DOCUMENTS

| | | | |
|---|---|---|---|
| 4,400,655 A | 8/1983 | Curtiss et al. | |
| 4,469,997 A | 9/1984 | Curtiss et al. | |
| 4,528,898 A | 7/1985 | Sharp et al. | |
| 4,706,553 A | 11/1987 | Sharp et al. | |
| 4,773,311 A | 9/1988 | Sharp | |
| 4,893,551 A | 1/1990 | Sharp | |
| 5,117,746 A | 6/1992 | Sharp | |
| 5,240,455 A | 8/1993 | Sharp | |
| 5,246,668 A | 9/1993 | MacCullum et al. | |
| 5,267,897 A | 12/1993 | Drees | |

(Continued)

FOREIGN PATENT DOCUMENTS

| | | |
|---|---|---|
| CN | 101194129 A | 6/2008 |
| CN | 103148560 A | 6/2013 |

(Continued)

*Primary Examiner* — Herbert K Roberts
(74) *Attorney, Agent, or Firm* — LaMorte & Associates PC

(57) ABSTRACT

A system and method for simultaneously running a plurality of air quality sensor units using a centralized station and software to test for field performance upon factory return from field installations, automatically identify preventative maintenance requirements, and automatically calibrate the sensor units and generate quality metric reporting. The centralized station and software include a computer, a manifold, tubes, and cables. A test gas is supplied, wherein the manifold distributes the test gas. Once powered and supplied with test gas, the sensor units are tested simultaneously. The computer runs software that compares the test data collected from the sensor units to determine if any of the sensor units fail standards or produce data that deviates from a mean average range. Sensor units that do not require maintenance are calibrated using test gasses to generate calibration coefficients which are stored within the sensors' firmware.

13 Claims, 6 Drawing Sheets

(56) References Cited

U.S. PATENT DOCUMENTS

| | | |
|---|---|---|
| 5,292,280 A | 3/1994 | Janu et al. |
| 5,293,771 A | 3/1994 | Ridenour |
| 5,304,093 A | 4/1994 | Sharp et al. |
| 5,385,505 A | 1/1995 | Sharp et al. |
| 5,406,073 A | 4/1995 | Sharp et al. |
| 5,435,779 A | 7/1995 | Sharp et al. |
| 5,544,809 A | 8/1996 | Keating et al. |
| 5,545,086 A | 8/1996 | Sharp et al. |
| 5,831,848 A | 11/1998 | Rielly et al. |
| 6,116,375 A | 9/2000 | Lorch et al. |
| 6,125,710 A | 10/2000 | Sharp |
| 6,137,403 A | 10/2000 | Desrochers et al. |
| 6,241,950 B1 | 6/2001 | Veelenturf et al. |
| 6,252,689 B1 | 6/2001 | Sharp |
| 6,425,297 B1 | 7/2002 | Sharp |
| 6,442,639 B1 * | 8/2002 | McElhattan ........... G16H 40/67 710/305 |
| 6,457,437 B1 | 10/2002 | Frasier et al. |
| 6,609,967 B2 | 8/2003 | Sharp et al. |
| 6,790,136 B2 | 9/2004 | Sharp et al. |
| 7,216,556 B2 | 5/2007 | Desrochers et al. |
| 7,302,313 B2 | 11/2007 | Sharp et al. |
| 7,360,461 B2 | 4/2008 | Desrochers et al. |
| 7,389,158 B2 | 6/2008 | Desrochers et al. |
| 7,389,704 B2 | 6/2008 | Desrochers et al. |
| 7,415,901 B2 | 8/2008 | Desrochers et al. |
| 7,421,911 B2 | 9/2008 | Desrochers et al. |
| 8,147,302 B2 | 4/2012 | Desrochers et al. |
| 9,109,981 B2 | 8/2015 | Sharp |
| 9,964,470 B2 | 5/2018 | Sharp |
| 2004/0055359 A1 * | 3/2004 | Ketler ................ G01N 33/0006 702/100 |
| 2005/0056079 A1 | 3/2005 | Nagy et al. |
| 2006/0173580 A1 | 8/2006 | Desrochers et al. |
| 2006/0234621 A1 | 10/2006 | Desrochers |
| 2014/0260692 A1 | 9/2014 | Sharp |
| 2019/0128550 A1 | 5/2019 | Campos |
| 2021/0088247 A1 | 3/2021 | Kriss |
| 2022/0099641 A1 | 3/2022 | Desrochers |

FOREIGN PATENT DOCUMENTS

| | | | |
|---|---|---|---|
| CN | 203215922 U | 9/2013 | |
| CN | 203336777 U | 12/2013 | |
| WO | WO 94/09324 | 4/1994 | |
| WO | WO 02/41095 | 5/2002 | |
| WO | WO-2022049378 A1 * | 3/2022 | ............. G01N 15/06 |

* cited by examiner

SYSTEM AND METHOD FOR SIMULTANEOUSLY EXAMINING, MAINTAINING AND CALIBRATING MULTIPLE SENSORS AND SENSOR TYPES

BACKGROUND OF THE INVENTION

1. Field of the Invention

In general, the present invention relates to systems that are used to test, calibrate, and provide sensor component maintenance information for air quality sensors. More particularly, the present invention relates to systems that can test, calibrate, and provide sensor component maintenance information for multiple sensors and sensor types.

2. Prior Art Description

Many buildings have complex heating, ventilation, and air-conditioning (HVAC) systems that control the environment within the building. Proper temperature control and ventilation control within a building is critical to the health and comfort of the people within a building. Furthermore, there are local, state, and federal regulations regarding minimum ventilation requirements to ensure air quality standards are maintained in large buildings and confined public spaces. Such regulations typically focus on carbon dioxide concentrations, presence of particulate matter, and presence of chemical pollutants and/or other harmful contaminants in the air. There are also industry standards for air quality in specialized environments, such as clean rooms, operating rooms, laboratories, and the like.

In order to meet air quality standards, many building HVAC systems utilize an air quality monitoring system. The air quality monitoring system samples the air from different points within the building and actively measures those samples using electronic sensors. Some of the most common tests for air quality include measuring carbon dioxide levels, measuring relative humidity levels, and measuring concentrations of particulate matter and chemical pollutants in the ambient air. Carbon dioxide is an excellent indicator of proper ventilation for a building. Carbon dioxide is typically found in outside air at concentrations between 400 PPM and 500 PPM. Exhaled breath of an average office worker adds carbon dioxide to the environment of the building at an approximate rate of 0.01 cubic feet per minute. Variations in carbon dioxide levels in a building can therefore be used to determine the number of individuals in a building, since the level of carbon dioxide in a space is directly related to the number of people in the space. Thus, proper ventilation levels in a densely occupied building can be well controlled simply by monitoring changes in carbon dioxide concentrations. Furthermore, since the levels of carbon dioxide are indicative of the degree of external air ventilation, the levels of carbon dioxide also correspond to the level of outdoor pollutants and particulate matter being introduced into the environment of the building.

Many buildings have different floors and different rooms on each floor. Each floor and many of the rooms require heating, ventilation, and air conditioning. Furthermore, in many buildings, such as hotels, each room has its own HVAC controls. Accordingly, in order to properly control the quality of air in a building, there must be a large number of air sampling points throughout the building. One solution to sampling air throughout a building has been to capture air samples from a wide selection of collection points and funnel those samples to a common suite of sensors. In this manner, a limited number of sensors need be used to monitor air quality captured at various points throughout a large building. Such systems are exemplified by U.S. Pat. Nos. 9,964,470 and 9,109,981 to Sharp.

Even though air samples are channeled to a centralized suite of sensors, different types of sensor units are used to monitor different parameters, such as carbon dioxide concentrations, temperature, relative humidity, particulate matter concentrations, and the like. Each of these sensor units must be initially tested and calibrated upon manufacture. Additionally, the sensor units must be periodically re-tested, cleaned, replaced, and/or recalibrated using sophisticated equipment. This adds significantly to the costs of operating and maintaining a sophisticated HVAC system in a building.

A need therefore exists for a system that simplifies the examining, maintenance, and calibration of air quality sensors that are used to monitor air quality in a building. This need is met by the present invention as described and claimed below.

SUMMARY OF THE INVENTION

A system and method for simultaneously examining, calibrating, and maintaining a plurality of air quality sensor units. Air quality sensor units are taken to a centralized station. The centralized station contains receptacles for receiving and retaining a plurality of air quality sensor units. The centralized station contains a computer, a manifold, tubes, and cables. At least one of the tubes and at least one of the cables are connected to each of the air quality sensor units. A test gas is then supplied to the manifold, wherein the manifold distributes the test gas to the air quality sensor units via the tubes.

Sensor units are analyzed when received from field to determine quality metrics along with the condition of the sensor components. Sensor units with failed components or components that are beyond their age limit are flagged for maintenance and/or replacement. Once powered and supplied with test gas, the air quality sensor units are tested simultaneously. During testing, the sensor units produce test data that is analyzed by the computer. The computer runs testing software that analyzes the test data collected from the air quality sensor units to determine if any of the sensor units fail performance specifications standards or produce data that deviates from a mean average range. Applicable sensor units that do not require additional maintenance are then run using applicable test gasses to generate calibration coefficients which are stored within the sensors' firmware. The output of the calibrated sensors is recorded within a calibration report. Calibrated sensors can then be run with clean air for multiple days to check for measurement drift and/or reading inconsistencies.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention sensor examining and calibration system can be embodied in many ways, only two exemplary embodiments are illustrated. The exemplary embodiments are being shown for the purposes of explanation and description. The exemplary embodiments are selected in order to set forth some of the best modes contemplated for the invention. The illustrated embodiments, however, are merely exemplary and should not be considered as limiting when interpreting the scope of the appended claims.

Figure 1:
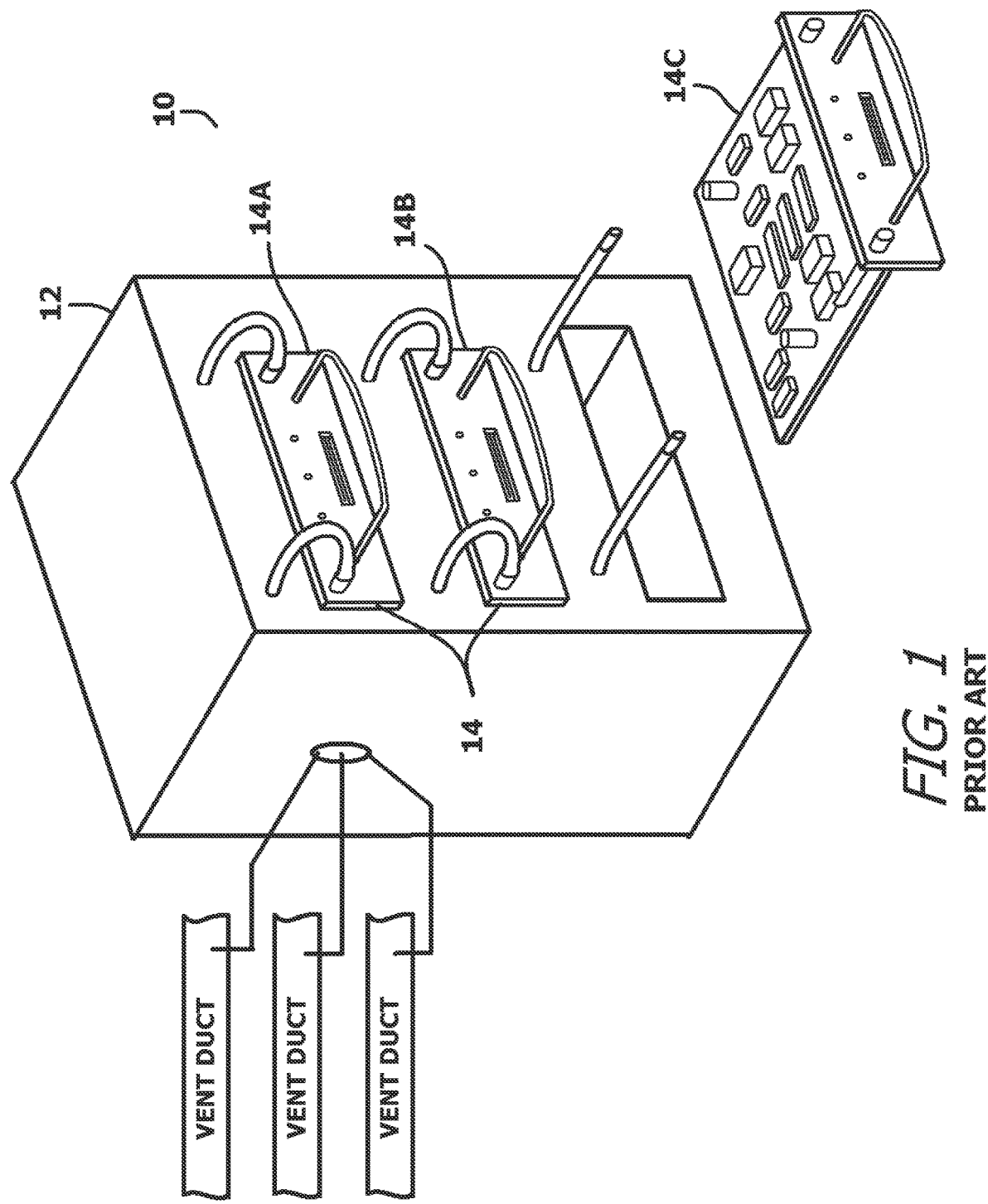
FIG. 1 shows a prior art air quality monitoring control center containing sensor units.

Referring to FIG. 1, the control center 10 for a prior art sensor suite 12 is shown. The sensor suite 12 contains a plurality of sensor units 14. Within the sensor suite 12, the sensor units 14 are selectively exposed to air samples that are collected from various test points throughout a building. Depending upon the location and application, a variety of sensor units 14 can be utilized. That is, there are sensor units 14 of different types to monitor different environmental factors. One type of sensor unit 14A may detect carbon dioxide concentrations. A second type of sensor unit 14B may detect relative humidity. A third type of sensor unit 14C may detect concentrations of particulate matter. Other types of sensor units can include sensors for detecting various gasses, such as carbon monoxide, Total Volatile Organic Compounds (TVOCs), and the like. The sensor units 14 are electronic assemblies or electro-optical assemblies, depending upon the type of sensor unit and its purpose. The sensor units 14 can be selectively detached from the sensor suite 12 for testing, recalibration, repair, and replacement.

Figure 2:
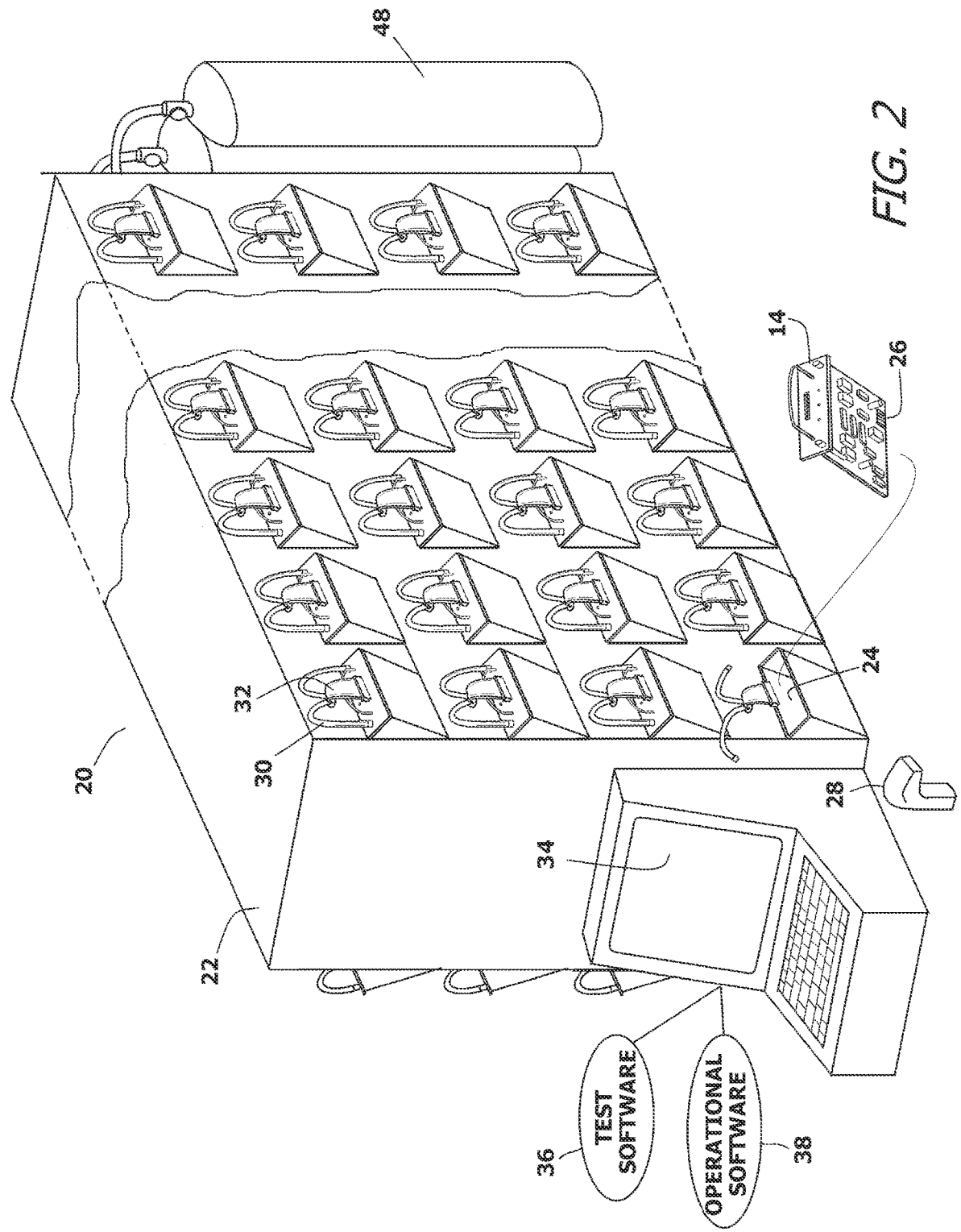
FIG. 2 shows the exemplary embodiment of a centralized station for examining and calibrating air quality sensor units.
Figure 3:
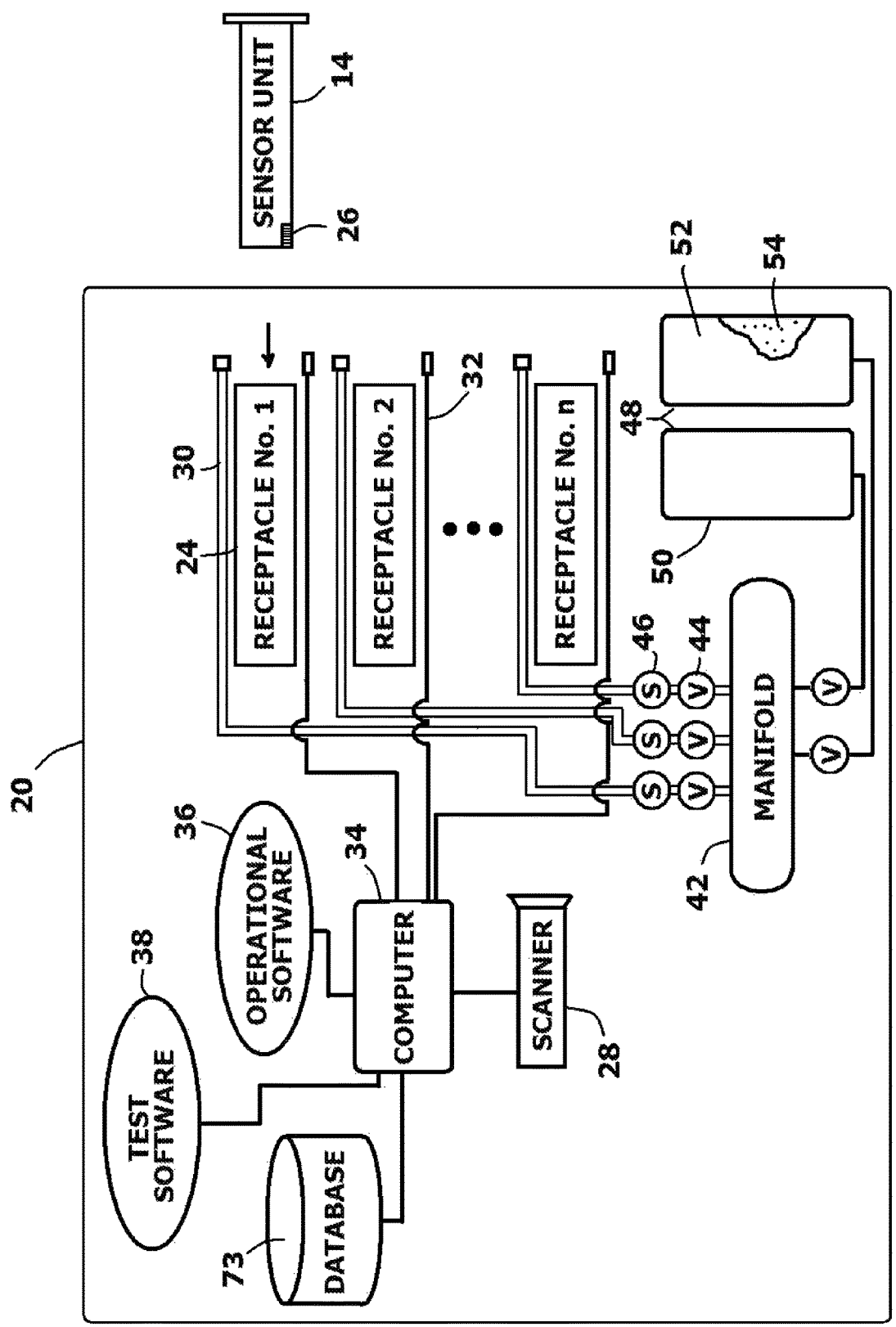
FIG. 3 shows a schematic for the exemplary centralized station of FIG. 2.

Referring to FIG. 2 and FIG. 3, in conjunction with FIG. 1, a centralized station 20 is disclosed for examining and calibrating any and all of the sensor units 14 that can be used in the examining and calibrating suite 12 of FIG. 1. The centralized station 20 has a test and calibration stand 22. The test and calibration stand 22 contains a plurality of receptacles 24 for receiving and retaining various sensor units 14. The receptacles 24 can be universal, wherein one size fits all sensor units 14. Alternatively, the receptacles 24 can be specific to receive only the sensor units 14 of a particular type or particular make and model.

Each sensor unit 14 can contain an electronic identifier that is integrated into the electronics of the sensor unit 14, wherein the centralized station 20 automatically reads the electronic identifier code 26 that is generated. In either scenario, the identifier 26 enables each of the sensor units 14 to be uniquely identified and tracked. The identifier 26 also enables the centralized station 20 to identify the sensor unit 14, its type, make and model, its position in the test stand 22, component level information for maintenance and quality metric purposes, and its test history.

In each receptacle 24, a sensor unit 14 is attached to both a gas tube 30 and to a cable 32. The gas tube 30 and the cable 32 are terminated in the same manner as the tubes and cables used in the sensor suite 12. In this manner, if there are any problems with the connector couplings on the sensor unit 14, the problem is made known before the sensor unit 14 is shipped to a location.

The cables 32 provide power and electrically connect the sensor units 14 to a computer 34. The computer 34 contains the same operational software 36 that is used in the sensor suite 12 on location. The computer 34 also has the ability to run specialized software 38 that is only used for testing, calibrating, and providing component maintenance information for the sensor units 14 in the centralized station 20. The specialized test software 38 also tests the voltage, resistance, capacitance, signal strength, signal noise and operational speed of various components and circuits contained within the sensor unit 14, depending on the sensor type. This electrical testing ensures that the sensor unit 14 meets the electrical and measurement specifications of its design. If any sensor unit 14 fails the electrical or measurement test cycle, a failed condition is forwarded to the computer 34. The computer 14 generates a log entry for the sensor unit 14 that identifies the sensor unit 14 that failed and the reason for failure. The failed sensor unit 14 can then be repaired and retested.

The gas tubes 30 that connects to the sensor units 14 supply test gases to the sensor units 14. The test gases supplied to the sensor unit 14 depend upon what the sensing unit 14 is designed to detect. All gas tubes 30 connect to a common supply manifold 42. Regulator valves 44 and flow volume sensors 46 are provided between the manifold 42 and the sensor units 14. The flow volume sensors 46 provide data to the computer 34. The computer 34 utilizes the data to control the regulator valves 44, therein ensuring that each of the gas tubes 30 is providing the same volume of test gas to the sensor units 14 at the same temperatures and pressures.

The manifold 42 is connected to one or more portable gas supply tanks 48. The gas supply tanks 48 include at least one clean air supply tank 50 and a test gas supply tank 52. The clean air supply tank 50 contains air that is filtered. The clean air supply tank 50 can be used to test for measurement anomalies and to flush residual test gas out of the manifold 42 and gas tubes 30. To test for measurement anomalies, the flow of clean air from the clean air supply tank 50 is used to pressurize the manifold 42. The regulator valve 44 supplies the clean air to the sensor units 14 at the proper pressure. The levels of contaminations in the clean air are known. Accordingly, test data is collected from each of the sensor units 14. If any of the sensor units 14 fails to measure within the required accuracy specifications, then that sensor unit 14 gets flagged to be repaired and/or recalibrated. Since multiple sensor units 14 of the same type are being tested simultaneously, the data outputs of all the sensor units 14 can be compared. The output data from all the sensor units 14 can be used to determine a mean average range. If a particular sensor unit 14 passes but produces data inconsistent with the mean average of the other sensor units 14, then secondary tests can be run to determine what components and/or circuits are causing the inconsistencies. In this manner, problematic internal components can be diagnosed and replaced before any more such components are introduced into the product stream. If data readings from various sensor units 14 vary slightly, the sensor units 14 can be electronically assigned different "zero" readings that correspond to the readings produced for the baseline gas. The zero readings are used to calibrate the sensor units 14.

After the various sensor units 14 are zeroed using clean air, the test gas supply tank 52 connects to the manifold 42. The test gas supply tank 52 contains a test gas 54 with a known concentration of the measured component. For example, air with 2500 PPM of carbon dioxide or air with 5 PPM of isobutylene can be used as a test gas. The test gases are mixed to specifications by a commercial gas supplier. The test gas 54, along with additional test gases as required, is used to generate calibration coefficients specific for each individual sensor as well as to determine the accuracy of the sensor units and adjust the coefficients as needed. The test gas 54 is used to pressurize the manifold 42. The regulator valve 44 supplies the test gas 54 to the sensor units 14 at the proper pressure. The measured component concentration in the test gas 54 is known. Test data is collected from each of the sensor units 14. If any of the sensor units 14 measures the test gas inaccurately, then that sensor unit 14 is repaired and/or recalibrated. Since multiple sensor units 14 of the same type are being tested together simultaneously, the data outputs of all the sensor units 14 can be compared. If the different sensors units 14 measured produce a variety of readings, then additional tests can be run to determine what components and/or circuits are causing the inconsistencies. Likewise, if one of the sensor units 14 passes the test, but exhibits data outside a mean average range, then that sensor unit 14 can be further evaluated. In this manner, problematic internal components can be diagnosed and replaced before any more such components are introduced into the product stream. If the data readings from the various sensor units 14 vary slightly, the sensor units 14 can be electronically calibrated to produce readings that correspond to the known concentrations of the test gas. Once calibrated, the sensor units 14 can be run with clean air for multiple days with the readings being logged to look for measurement drift and reading inconsistencies. The sensors are then removed from the test and calibration assembly.

Figure 4:
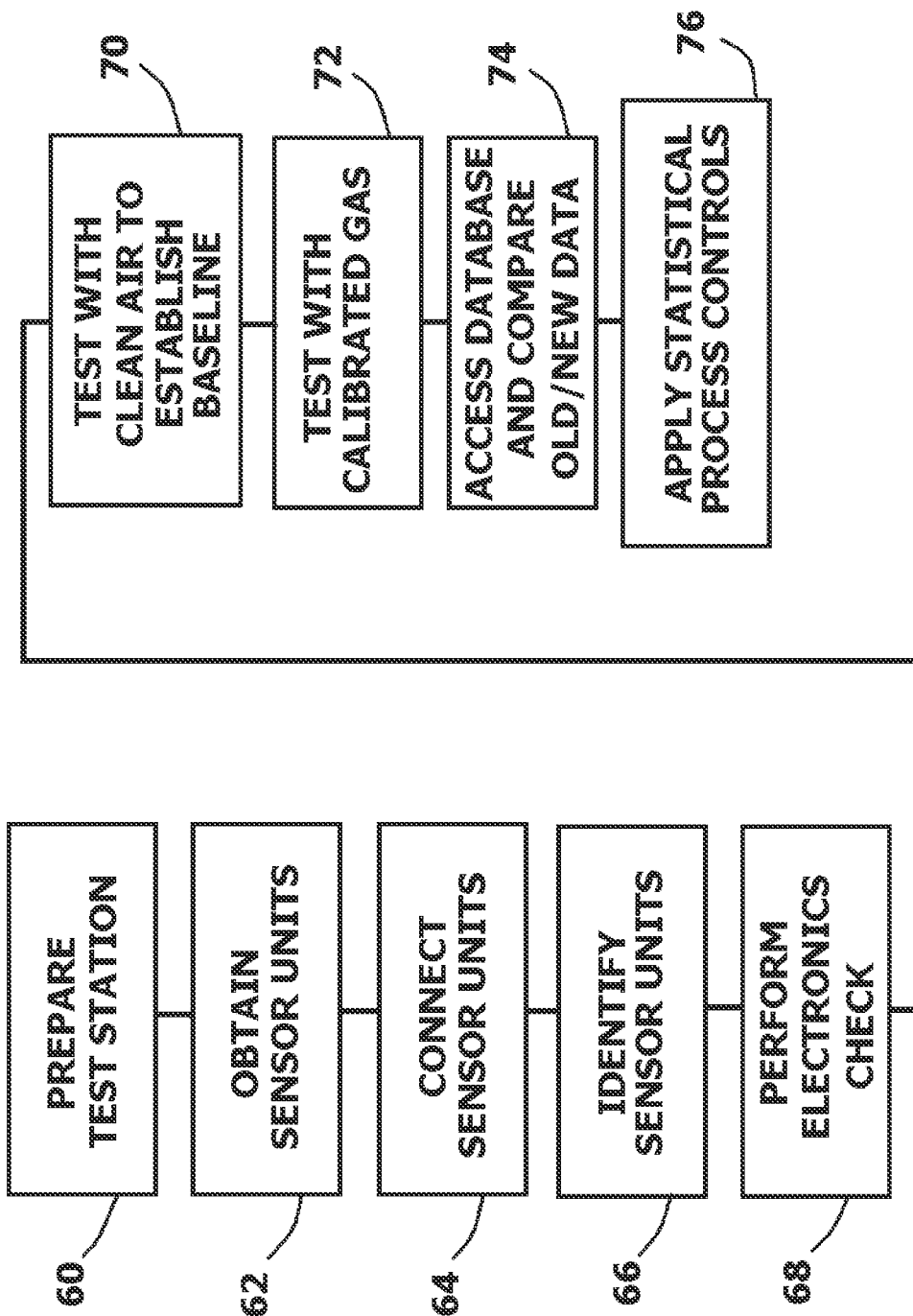
FIG. 4 shows a block diagram outlining an examining and calibration methodology utilized by the exemplary centralized station.

Referring to FIG. 4 in conjunction with FIG. 2 and FIG. 3, the examining and calibration sequence is summarized. The centralized station 20 is first prepared for testing by attaching the appropriate supply tanks 48 to the centralized station 20 that will be needed to conduct the selected testing. See Block 60. The sensor units 14 are obtained, either new from an assembly line or used from a prior application. See Block 62. The sensor units 14 are electrically and pneumatically connected to the centralized station 20. See Block 64. The sensor units 14 are scanned or otherwise identified by the computer 34 of the centralized station 20. See Block 66.

Once connected, the centralized station 20 first performs an electronics' check on the sensor units 14 to ensure that various components and or circuits within the sensor units 14 meet specifications. See Block 68. If the sensor units 14 pass the initial electronics check, then the sensor units 14 are tested using at least two separate gasses. One gas is clean air to establish a baseline data set for each sensor unit 14. See Block 70. The second gas is a gas containing the measured component to establish a second active data set for each sensor unit 14. See Block 72. The data sets for each sensor unit 14 are collected and stored in an archive database 73. An "as-received" report is generated where various sensor components will be flagged for replacement due to age or their test performance. In this manner, should the same sensor units 14 be tested in the future, the differences in the data sets can be compared. See Block 74. Using statistical process controls, a rate of data drift can be ascertained for each of the sensor units 14. The rate of data drift can be used to predict a failure date for each sensor unit 14. If such a drift in data is detected, the sensor units 14 can be scheduled to be replaced long before failure occurs. See Block 76.

Figure 5:
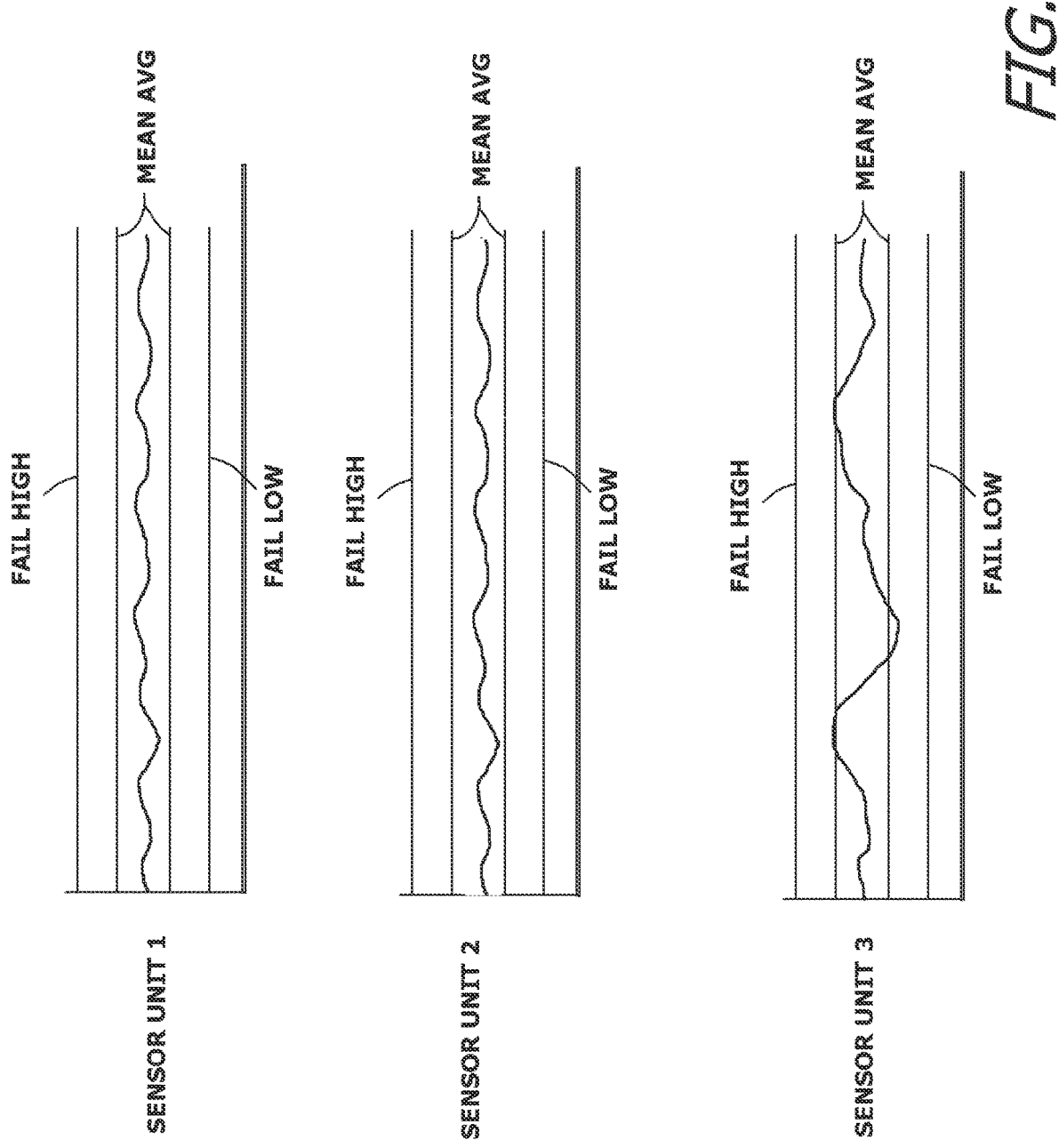
FIG. 5 shows exemplary graphs of data to illustrate sensor readings within a mean average range.

Since the centralized station 20 tests multiple sensor units 14 simultaneously using the same test gases and utilizing the same testing conditions, useful data can be obtained by comparing test data generated by the various sensor units 14. Referring to FIG. 5, the test data from multiple sensor units 14 is shown. Using statistical process controls, the test data can be used to determine a mean average range 78. As can be seen, if most sensor data sets are similar and one set 79 is different, it can be concluded that the odd sensor unit is not functioning in the manner it should. Accordingly, the odd sensor unit 14 can be identified for further testing or replacement proactively.

Figure 6:
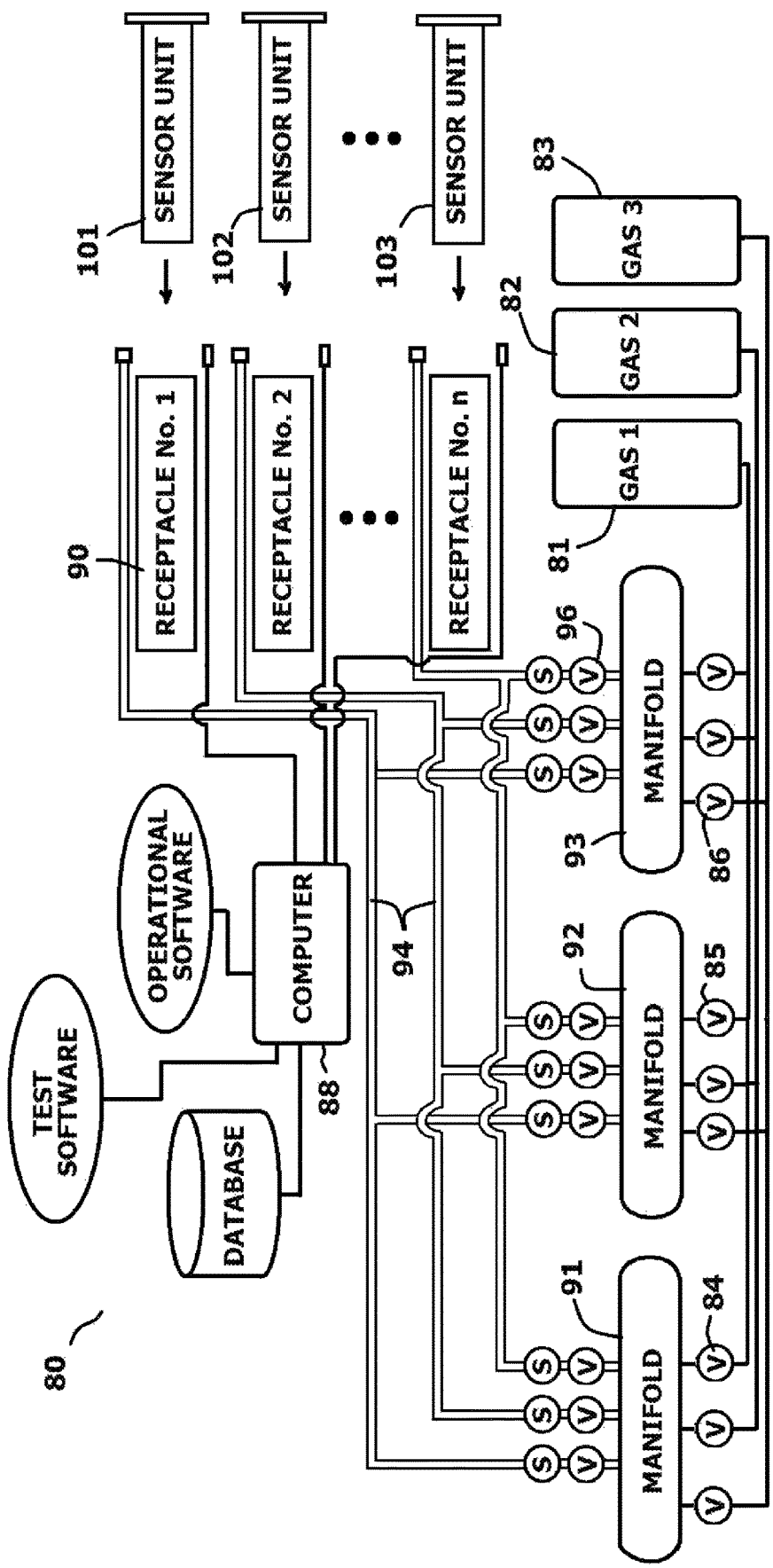
FIG. 6 shows a schematic for an alternate embodiment of a centralized station that tests and calibrates different types of sensor units simultaneously.

In the embodiment previously described, all the sensor units 14 in the centralized station 20 are of the same type and are tested using the same gases. This need not be the case. Referring to FIG. 6, a slight variation of a centralized station 80 is shown where multiple gas supply tanks 81, 82, 83 are connected to a corresponding number of manifolds 91, 92, 93. Each of the test gas supply tanks 81, 82, 83 has supply valves 84, 85, 86 that are controlled by a computer 88. Accordingly, any one or more of the gas supply tanks 81, 82, 83 can be activated at one time. Each of test receptacles 90 is connected to each of the manifolds 91, 92, 93 using branch tubes 94. Each branch tube 94 has a computer controlled valve 96 that is controlled by the computer 88.

Using this system, one of more of the gas supply tanks 81, 82, 83 can be individually directed to each of the test receptacles 90. In this manner, different test receptacles 90 can hold different sensor units 101, 102, 103 and the different sensor units 101, 102, 103 can be tested simultaneously.

The overall centralized station 80 can be made small enough to be transportable in a truck or van. In this manner, the centralized station 80 can be driven to a building that has a complex HVAC system. The various air quality sensors from that building can then be rapidly tested at the same time.

It will be understood that the embodiments of the present invention that are illustrated and described are merely exemplary and that a person skilled in the art can make many variations to those embodiments. All such embodiments are intended to be included within the scope of the present invention as defined by the claims.

What is claimed is:

1. A method for simultaneously examining and calibrating air quality sensor units, said method comprising:
    providing a plurality of air quality sensor units in need of testing and calibration, wherein each of said plurality of air quality sensor units has a unique electronic identifier and a unique test history;
    providing a centralized station that contains receptacles a manifold, tubes, and cables, wherein said receptacles receive and retain said plurality of air quality sensor units at a plurality of test positions on said centralized station;
    connecting at least one of said tubes and at least one of said cables to each of said plurality of air quality sensor units retained in one of said receptacles;
    providing a computer at said centralized station that has access to an archive database, wherein said archive database stores said unique test history for each of said plurality of air quality sensor units,
    wherein said computer electronically communicates with said plurality of air quality sensor units via said cables and reads said unique electronic identifier from each of said plurality of air quality sensor units as said plurality of air quality sensor units are attached to said cables;

supplying a test gas to said manifold, wherein said manifold distributes said test gas to said plurality of air quality sensor units in said receptacles via said tubes;

utilizing said computer to perform an electronics check test on said plurality of air quality sensor units that are connected to said cables in said receptacles, wherein said electronics check test produces electronics test data, calibrating said plurality of air quality sensor units utilizing said test gas, wherein said plurality of air quality sensor units produce gas test data that is supplied to said computer;

retrieving said unique test history for each of said plurality of air quality sensor units from said archive database using said unique electronic identifier for each of said plurality of air quality sensor units and comparing said unique test history of each said plurality of air quality sensor units to said electronics test data and said gas test data to determine a rate of data drift for each of said plurality of air quality sensor units; and identifying any of said plurality of air quality sensor units that have a rate of data drift indicative of impending failure.

2. The method according to claim 1, wherein said computer runs examining software that compares said test data collected from said plurality of air quality sensor units to determine if any of said plurality of air quality sensor units produce data that deviates from a mean average range.

3. The method according to claim 1, further including substituting clean air for said test gas and using said clean air to calibrate said plurality of air quality sensor units.

4. The method according to claim 1, further including pressure regulators for regulating pressure of said test gas in each of said tubes.

5. The method according to claim 4, wherein said pressure regulators are controlled by said computer.

6. The method according to claim 1, further including providing a scanner that scans and identifies each of said plurality of air quality sensors as said plurality of air quality sensors is placed into said receptacles.

7. A method for simultaneously examining and calibrating air quality sensor units of different types, said method comprising:

providing a centralized station that contains receptacles for receiving and retaining said air quality sensor units therein;

providing a plurality of manifolds that are separate and distinct from one another;

providing separate branch tubes that extend from each of said plurality of manifolds to each of said receptacles, wherein each of said branch tubes has a control valve;

providing a computer at said centralized station and cables that lead between said computer and each of said receptacles;

connecting at least one of said branch tubes and at least one of said cables to each of said air quality sensor units retained in one of said receptacles;

providing different test gas supplies and connecting said different test gas supplies to said plurality of manifolds so that each of said plurality of manifolds is supplied with a different test gas;

selectively operating said supply valves to selectively connect said plurality of manifolds with said air quality sensor units of different types, wherein each type of said air quality sensor units receives a different test gas from said plurality of manifolds; and simultaneously examining and calibrating said air quality sensor units, wherein said sensor units produce data that is analyzed by a computer.

8. The method according to claim 7, wherein said computer runs testing software that compares said data collected from said air quality sensor units of each different type to determine if any of said air quality sensor units produce data that deviates from a mean average.

9. The method according to claim 7, wherein at least one of said different test gas supplies is a clean air supply used for calibration of said plurality of air quality sensor units.

10. The method according to claim 7, further including pressure regulators for regulating pressure in each of said tubes.

11. The method according to claim 10, wherein said pressure regulators are controlled by said computer.

12. The method according to claim 7, further including identifying each of said plurality of air quality sensors and storing said data generated from each of said sensor units in an archive database that is accessible by said computer.

13. The method according to claim 7, further including providing a scanner that scans and identifies each of said air quality sensors as said air quality sensors are placed into said receptacles.

\* \* \* \* \*